(12) United States Patent
Maekubo

(10) Patent No.: US 10,856,883 B2
(45) Date of Patent: Dec. 8, 2020

(54) MEDICAL CLIP CARTRIDGE

(71) Applicant: KANEKA CORPORATION, Osaka (JP)

(72) Inventor: Naotake Maekubo, Okaya (JP)

(73) Assignee: KANEKA CORPORATION, Osaka (JP)

( * ) Notice: Subject to any disclaimer, the term of this patent is extended or adjusted under 35 U.S.C. 154(b) by 178 days.

(21) Appl. No.: 15/779,703

(22) PCT Filed: Nov. 8, 2016

(86) PCT No.: PCT/JP2016/083111
§ 371 (c)(1),
(2) Date: May 29, 2018

(87) PCT Pub. No.: WO2017/094455
PCT Pub. Date: Jun. 8, 2017

(65) Prior Publication Data
US 2019/0282240 A1 Sep. 19, 2019

(30) Foreign Application Priority Data

Nov. 30, 2015 (JP) ................................. 2015-233971

(51) Int. Cl.
*A61B 17/122* (2006.01)
*A61B 17/128* (2006.01)
(Continued)

(52) U.S. Cl.
CPC ............ *A61B 17/1222* (2013.01); *A61B 1/00* (2013.01); *A61B 17/122* (2013.01); *A61B 17/1285* (2013.01); *A61B 2017/00526* (2013.01)

(58) Field of Classification Search
CPC ... A61B 17/122; A61B 17/1222; A61B 50/30; A61B 17/128
See application file for complete search history.

(56) References Cited

U.S. PATENT DOCUMENTS 4,935,026 A * 6/1990 McFadden ......... A61B 17/1227
606/142
8,114,098 B2 * 2/2012 Kimura ................. A61B 10/04
606/139
(Continued)

FOREIGN PATENT DOCUMENTS

JP 2009-011769 A 1/2009
JP 3159939 U 6/2010
(Continued)

OTHER PUBLICATIONS

International Search Report (PCT/ISA/210) issued in PCT/JP2016/083111, dated Feb. 14, 2017.
(Continued)

*Primary Examiner* — Wade Miles
*Assistant Examiner* — Mohammed S Adam
(74) *Attorney, Agent, or Firm* — Birch, Stewart, Kolasch & Birch, LLP

(57) ABSTRACT

A medical clip cartridge (1) for connecting a medical clip (22) to a line member (25) having a connection part (31) on a distal part thereof, comprising an insertion port (2) for inserting a line member (25), an insertion path (3) extending distally from the insertion port (2), and a storing part (4) for storing a clip (22), that is connected to a distal end of the insertion path (3), wherein the insertion path (3) has a protrusion (5) projecting from an inner surface of the insertion path, and the protrusion (5) has a part whose top surface widens toward a distal end thereof and whose height from the inner surface of the insertion path increases toward the distal end.

19 Claims, 6 Drawing Sheets

(51) Int. Cl.
*A61B 1/00* (2006.01)
*A61B 17/00* (2006.01)

(56) References Cited

U.S. PATENT DOCUMENTS

| | | | | |
|---|---|---|---|---|
| 8,211,120 B2* | 7/2012 | Itoh | A61B 17/1285 | 606/142 |
| 8,262,678 B2* | 9/2012 | Matsuoka | A61B 17/1285 | 606/139 |
| 8,465,501 B2* | 6/2013 | Matsuoka | A61B 17/122 | 606/142 |
| 8,480,685 B2* | 7/2013 | Kimura | A61B 17/122 | 606/139 |
| 8,551,119 B2* | 10/2013 | Kogiso | A61B 17/122 | 606/142 |
| 8,939,997 B2* | 1/2015 | Martinez | A61B 17/08 | 606/142 |
| 9,585,674 B2* | 3/2017 | Terada | B21D 53/36 | |
| 9,687,248 B2* | 6/2017 | Satake | A61B 17/122 | |
| 2002/0045909 A1* | 4/2002 | Kimura | A61B 17/083 | 606/151 |
| 2005/0143767 A1* | 6/2005 | Kimura | A61B 17/1222 | 606/158 |
| 2005/0288711 A1* | 12/2005 | Fallin | A61B 17/0401 | 606/232 |
| 2007/0049947 A1* | 3/2007 | Menn | A61B 17/10 | 606/142 |
| 2007/0049950 A1* | 3/2007 | Theroux | A61B 17/128 | 606/142 |
| 2007/0049951 A1* | 3/2007 | Menn | A61B 17/128 | 606/142 |
| 2007/0112359 A1* | 5/2007 | Kimura | A61B 17/122 | 606/142 |
| 2007/0179530 A1* | 8/2007 | Tieu | A61B 17/0487 | 606/232 |
| 2007/0282355 A1* | 12/2007 | Brown | A61B 17/122 | 606/151 |
| 2008/0200756 A1* | 8/2008 | Okada | A61B 1/00133 | 600/106 |
| 2009/0228023 A1* | 9/2009 | Cui | A61B 17/122 | 606/142 |
| 2009/0318937 A1* | 12/2009 | Matsuoka | A61B 17/1227 | 606/143 |
| 2010/0217281 A1* | 8/2010 | Matsuoka | A61B 17/1222 | 606/143 |
| 2011/0245855 A1* | 10/2011 | Matsuoka | A61B 17/1285 | 606/157 |
| 2012/0046671 A1* | 2/2012 | Matsuoka | A61B 17/1285 | 606/143 |
| 2013/0072946 A1* | 3/2013 | Terada | A61B 17/122 | 606/142 |
| 2013/0211432 A1* | 8/2013 | Terada | A61B 17/122 | 606/151 |
| 2014/0081318 A1* | 3/2014 | Houser | A61B 17/0057 | 606/213 |
| 2015/0190136 A1* | 7/2015 | Cohen | A61B 17/122 | 606/143 |
| 2018/0333156 A1* | 11/2018 | Hayashi | A61B 1/00101 | |

FOREIGN PATENT DOCUMENTS

| | | |
|---|---|---|
| JP | 2014-188345 A | 10/2014 |
| JP | 2015-043858 A | 3/2015 |

OTHER PUBLICATIONS

Written Opinion (PCT/ISA/237) issued in PCT/JP2016/083111, dated Feb. 14, 2017.

* cited by examiner

MEDICAL CLIP CARTRIDGE

TECHNICAL FIELD

The present invention relates to a medical clip cartridge that is used for connecting a medical clip to a line member such as a wire or the like.

BACKGROUND ART

In a treatment using an endoscope, a medical clip device for conveying a medical clip attached to a distal part of a line member such as a wire or the like may be used in order to grip a tissue to be treated such as an affected area. In the case of performing the treatment, a clip device is inserted into a forceps channel from a forceps port of the endoscope and the clip is conveyed to a tissue to be treated, whereby a procedure using the clip can be performed in the patient's body. In many cases, a plurality of medical clips are used during one operation, and it is necessary to attach a new clip to the clip device every time each clipping operation is performed. However, the size of the medical clip is very small, at most about 1 cm, so that it is difficult to attach the clip by hand. It becomes especially difficult for those who are unskilled or those who wear sterilized gloves. Meanwhile, since the act of attaching the clip is performed during the operation, it is desirable to be done accurately and promptly. Therefore, in order to facilitate the act of attaching the clip to the line member, a clip cartridge is used for a connection aid.

As a clip cartridge, for example, Patent Literature 1 discloses a clip attachment tool (a clip cartridge) comprising a clip storing part for storing a clip and a hook guide hole for guiding a connection hook to a connection part of the clip from its rear, wherein the hook guide hole has a cross-sectional shape which gradually changes to a flat shape so that an orientation of the connection hook inserted therein is correct and is to be capable of engaging with or disengaging from the connection part of the clip in the direction from a rear end port toward a boundary part with the front clip storing part. Patent Literature 2 discloses a clip cartridge for connecting a connection part to a base end of a clip, comprising a storing part that is located inside the clip cartridge and stores the clip, and an insertion hole which goes through from an outer surface of the clip cartridge as an inlet side to the storing part as an outlet side and which the connection part is inserted into, wherein a projection strip extending from the inlet side to the outlet side of the insertion hole is formed.

CITATION LIST

Patent Literature

PATENT LITERATURE 1
Japanese Unexamined Laid-open Patent Application Publication No. 2009-011769
PATENT LITERATURE 2
Japanese Unexamined Laid-open Patent Application Publication No. 2014-188345

SUMMARY OF INVENTION

Technical Problem

With use of the clip cartridges disclosed in Patent Literatures 1 and 2, it is possible to connect the connection hook or the connection part provided on the distal part of the line member to a clip while properly controlling the position in the axial rotation direction; and development of a clip cartridge which enables further improvement in efficiency is demanded. The present invention has been made in view of the above circumstances, and an object of the present invention is to provide a medical clip cartridge for connecting a medical clip to a line member having a connection part on a distal part thereof, that is capable of connecting the connection part to the clip while properly controlling the position of the connection part in the axial rotation direction.

Solution to Problem

A medical clip cartridge of the present invention which solves the above problem is a medical clip cartridge for connecting a medical clip to a connection part of a line member in which the connection part is provided on a distal part of the line member, comprising an insertion port for inserting a line member, an insertion path extending distally from the insertion port, and a storing part for storing a clip, that is connected to a distal end of the insertion path, wherein the insertion path has a protrusion projecting from an inner surface of the insertion path, and the protrusion has a part whose top surface widens toward the distal end thereof and whose height from the inner surface of the insertion path increases toward the distal end.

In the medical clip cartridge of the present invention, since the insertion path for inserting a line member is provided with a protrusion which has a part whose top surface widens toward the distal end and whose height from the inner surface of the insertion path increases toward the distal end, the connection part of the line member comes into contact with the protrusion in inserting the line member into the insertion path, whereby an angle or a position of the connection part can be properly controlled. Therefore, by using the medical clip cartridge of the present invention, the direction of the connection part provided on the distal part of the line member can be properly controlled, and the connection of the line member to the clip is easily performed.

It is preferred that the protrusion has a first lateral surface and a second lateral surface provided such that distance therebetween increases toward the distal end, and an angle between the first lateral surface and an extending direction of the insertion path is larger than an angle between the second lateral surface and the extending direction of the insertion path. By forming the first lateral surface and the second lateral surface on the protrusion in this manner, the probability of the connection part traveling along the first lateral surface becomes higher than the probability of the connection part traveling along the second lateral surface when the connection part hits a proximal tip of the protrusion. Therefore, in inserting the line member into the insertion path, the connection part tends not to be caught by the proximal tip of the protrusion, and so it proceeds smoothly further to a distal part of the insertion path.

It is preferred that the insertion path has only one protrusion. In the clip cartridge of the present invention, it is possible to properly control an angle with respect to an axial rotation direction and a position of the connection part by providing only the one protrusion. Therefore, the clip cartridge can be configured in a simple manner.

It is preferred that the insertion path has a tapered part positioned distal to the protrusion and being narrower in a height direction of the protrusion toward a distal end thereof. By providng the tapered part on the distal part of the insertion path, the distal part of the connection part fits into the tapered part in inserting the line member into the insertion path and the connection part is easily connected to the clip placed in the storing part properly.

It is preferred that the protrusion is pushable in a direction opposite to a projecting direction thereof. By forming the protrusion in this manner, the protrusion is pushed in the direction opposite to the projecting direction when the connection part comes into contact with the protrusion, so that the traveling direction of the connection part is not shifted a lot and the line member can be inserted further to the distal part of the insertion path. As a result, it is possible to reliably connect the connection part to an appropriate position of the clip.

It is preferred that the protrusion is removable from the insertion path. By forming the protrusion removable from the insertion path, a clip device in which the line member is connected with the clip can be easily taken out from the clip cartridge.

It is preferred that the clip cartridge includes a cartridge body and a cartridge cover, the cartridge body has a groove for forming the insertion path and a recessed part for forming the storing part, and the insertion port, the insertion path and the storing part are respectively formed by covering the cartridge body with the cartridge cover. By constructing the clip cartridge in this way, the clip cartridge is easily manufactured, and it becomes easy to set the clip in the clip cartridge and take out the clip device in which the line member is connected with the clip from the clip cartridge.

It is preferred that the connection part is formed such that a distal part is widened in a direction perpendicular to an axis of the line member. By forming the connection part in this manner, an angle with respect to the axial rotation direction or a position of the connection part is likely to be controlled properly when the connection part comes into contact with the protrusion in inserting the line member into the insertion path. The connection part further preferably has an inclined portion whose thickness increases toward a proximal end thereof; and in this case, the connection part is easily axially rotated also when the inclined portion contacts the protrusion.

In the clip cartridge of the present invention, a clip may be stored in the storing part. When the clip is stored in the storing part in advance, the connection of the line member with the clip is easily achieved by inserting the line member into the insertion port of the clip cartridge.

The present invention also provides a method for manufacturing a medical clip device using the clip cartridge of the present invention. A method for manufacturing a medical clip device of the present invention comprises the steps of: placing a clip in the storing part of the clip cartridge; and inserting a line member having a connection part on a distal part thereof into the insertion path of the clip cartridge to connect the connection part to the clip. In the case where a clip is stored in the storing part in advance, the step of placing a clip in the storing part of the clip cartridge can be omitted.

Advantageous Effects of Invention

In the medical clip cartridge of the present invention, since the insertion path for inserting a line member is provided with a protrusion which has a part whose top surface widens toward the distal end and whose height from the inner surface of the insertion path increases toward the distal end, the connection part of the line member comes into contact with the protrusion in inserting the line member into the insertion path, whereby an angle or a position of the connection part can be properly controlled. Therefore, by using the medical clip cartridge of the present invention, the direction of the connection part provided on the distal part of the line member can be properly controlled, and the connection of the line member to the clip is easily performed.

DESCRIPTION OF EMBODIMENTS

Figure 1:
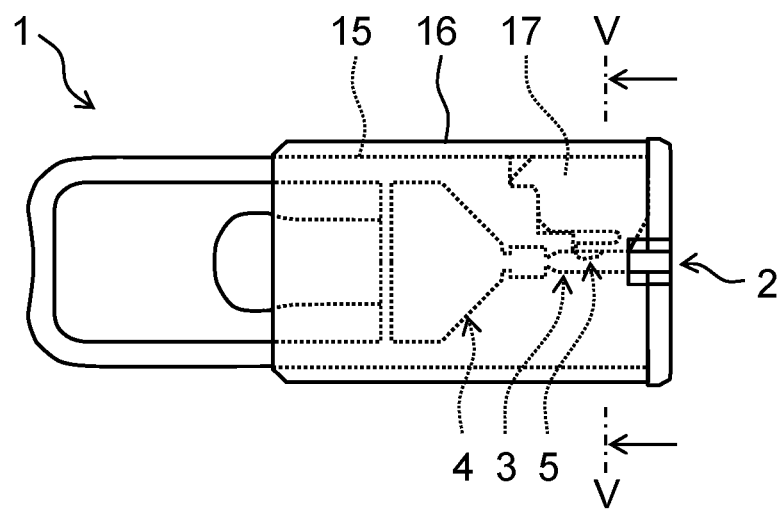
FIG. 1 shows a plan view of a clip cartridge.

The present invention relates to a medical clip cartridge for connecting a medical clip to a connection part of a line member in which the connection part is provided on a distal part of the line member. The clip cartridge of the present invention is used for connecting a clip to a line member when performing a treatment using a clip device with an endoscope. By inserting the clip device having the clip attached thereto into a forceps channel from a forceps port of the endoscope and conveying the clip to a tissue to be treated, treatment by the clip is able to be performed in the patient's body. A clip device with which the cartridge of the present invention can be used includes at least a clip and a line member, and the line member includes at least a connection part and a line member body.

Hereinafter, the present invention will be specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

Figure 2:
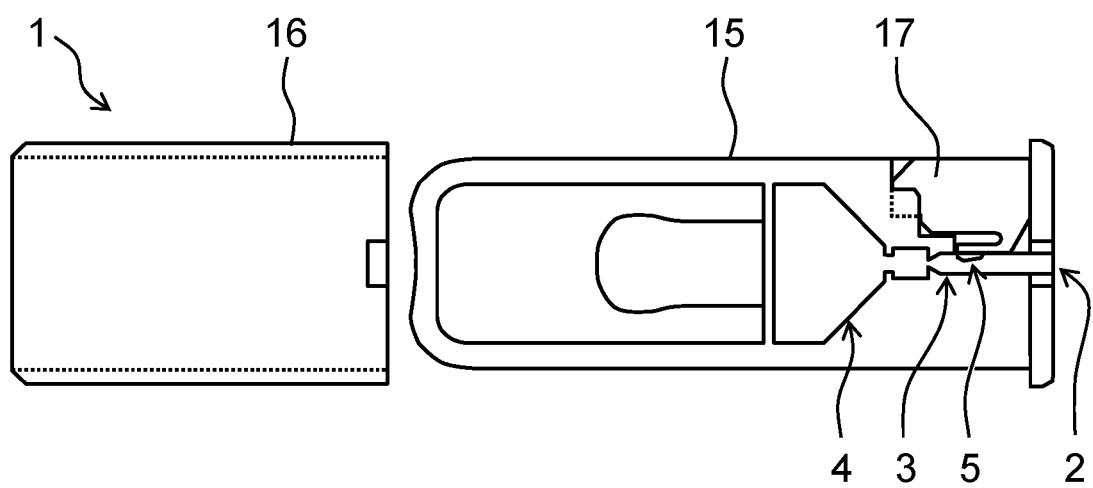
FIG. 2 shows a plan view of the clip cartridge shown in FIG. 1 where a cover is removed.
Figure 3:
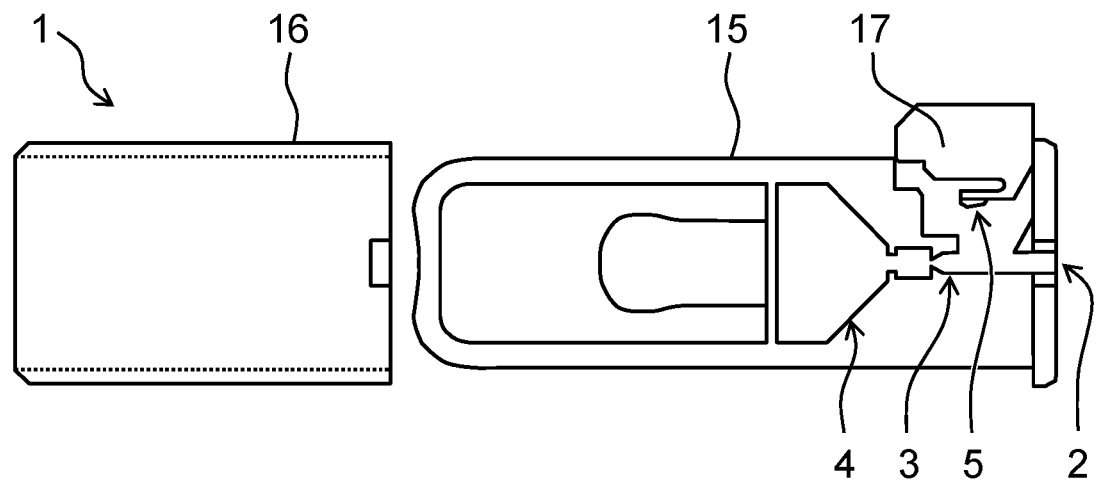
FIG. 3 shows a plan view of the clip cartridge shown in FIG. 2.
Figure 4:
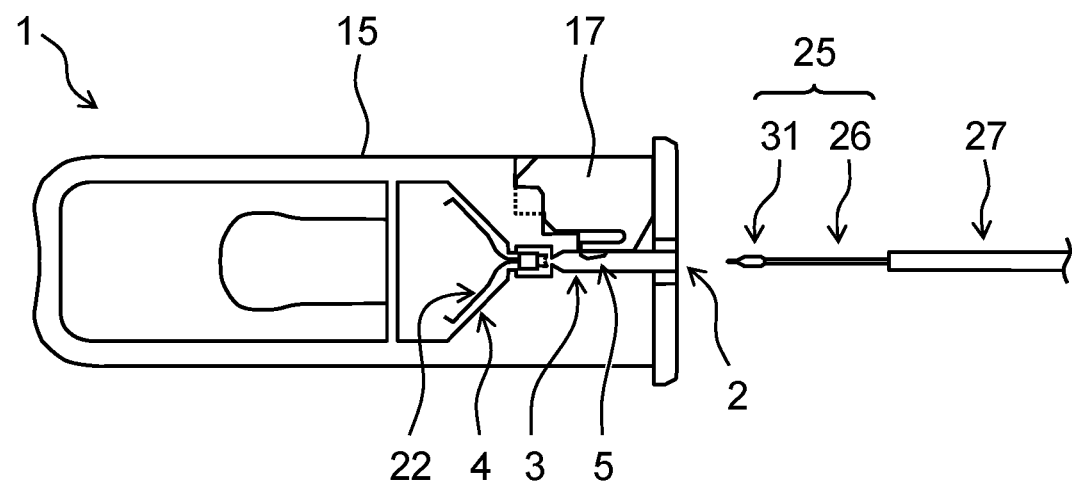
FIG. 4 shows a clip cartridge and a clip device and shows a plan view in which the cover of the clip cartridge is omitted.

FIGS. 1 to 4 show plan views of a medical clip cartridge. FIG. 1 represents a clip cartridge in the use state, FIG. 2 represents the clip cartridge shown in FIG. 1 in the state where a cover is removed, and FIG. 3 represents the clip cartridge shown in FIG. 2 in the state where a regulation member is further removed from an insertion path. FIG. 4 represents a clip cartridge body in the state where a clip is placed. When connecting the clip to the line member using the clip cartridge, a cover is attached to the clip cartridge body shown in FIG. 4 to be used.

Figure 9:
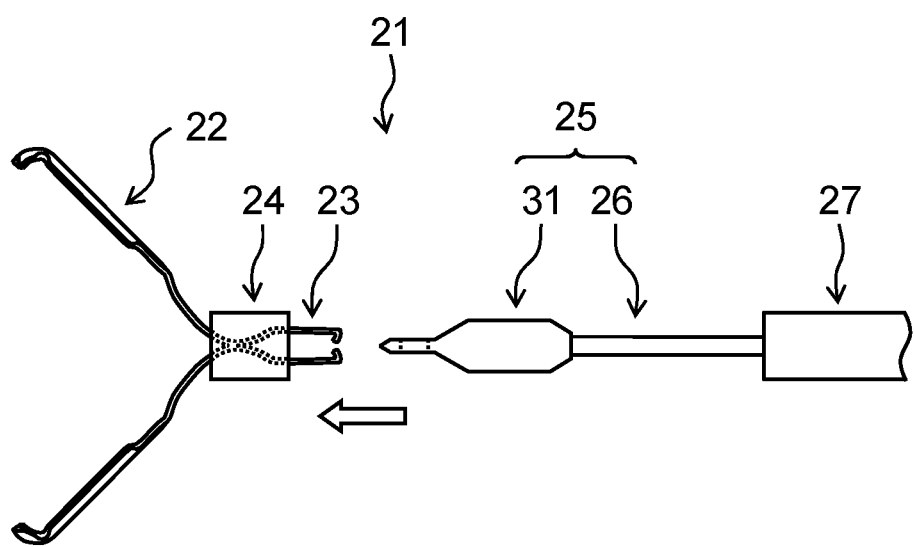
FIG. 9 shows a lateral view of a distal part of a clip device.

Prior to the explanation of a clip cartridge in detail, a configuration example of a clip device will be first explained with reference to FIGS. 4, 9 and 10. In FIG. 4, it is shown that a line member having a connection part on its distal part is inserted into a clip cartridge body in the state where a clip is stored; FIG. 9 shows a lateral view of a distal part of a clip device, where the clip is going to be connected to the line member; and FIG. 10 shows a perspective view of the connection part of the line member.

A clip device 21 is configured by connecting a proximal part of a clip 22 to a distal part of a line member 25. On the proximal part of the line member 25, an operation unit for operating the line member 25 is preferably provided, though it is not shown in the drawings. By operating the operation unit of the clip device 21 with an endoscope, the orientation of the clip 22 can be changed or opening-closing of the clip 22 can be controlled to grip an object with the clip 22. It is preferred that a connection part 31 is provided on a distal part of a line member body 26 of the clip device 21, thereby forming the line member 25. By connecting the connection part 31 of the line member 25 to the clip 22, the clip 22 can be attached to the distal part of the line member 25. The line member body 26 and the connection part 31 may be different objects from each other, or the distal part of the line member body 26 may form the connection part 31 and the clip 22 may be directly attached thereto. Here, the proximal direction of the clip device 21 or the line member 25 means a direction toward a hand of the user with respect to an axial direction (an extending direction) of the line member 25 and the distal direction of that means a direction opposite to the proximal direction (that is, a direction toward a target site).

The clip 22 is an instrument that pinches a target site such as a diseased part of an organ, grasps it to conduct counter-traction, or clips a target site for hemostasis, suturing or marking in performing an endoscopic treatment. The clip 22 is formed such that its distal part is able to be opened or closed with its proximal part as a fulcrum. The clip 22 is formed by, for example, bending a single metal plate into a U-shape or a V-shape, or by connecting two metal plates so as to face each other. The clip 22 has a base end part 23, which is to be connected to the connection part 31 of the line member 25, on the proximal part thereof.

Figure 10:
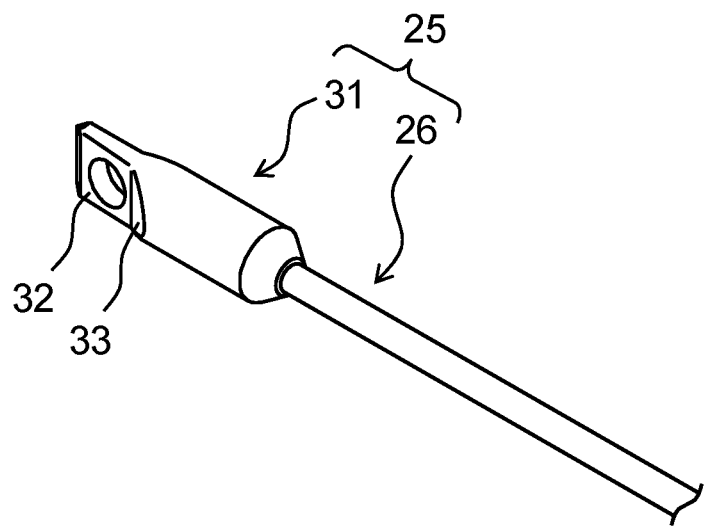
FIG. 10 shows a perspective view of a connection part of a clip device.

Various shapes can be selected for the base end part 23 of the clip 22 and the connection part 31 of the line member 25 as long as they can be connected to each other; and for example, as shown in FIGS. 9 and 10 where a claw is provided on the base end part 23 and an opening is provided on the connection part 31, a claw provided on one of the base end part 23 and the connection part 31 may engaged with an opening provided on the other of them, or claws are provided on both of them so that they are engaged with each other, whereby they can be connected to each other.

It is preferred that the clip 22 is provided with a tightening ring 24 surrounding the proximal part of the clip 22, and the clip 22 is preferably formed in such a manner that it can be closed when the tightening ring 24 is moved to the distal part of the clip 22 by, for example, bringing an inner tubular body 27 described below into contact with the tightening ring 24.

The clip 22 or the tightening ring 24 is preferably made of a material having high elasticity and biocompatibility. The clip 22 or the tightening ring 24 is preferably made of a stainless steel such as SUS 303, SUS 304 and SUS 631; Ni—Ti alloy; or the like, for example.

The line member 25 is formed in a linear shape and has the connection part 31 on the distal part thereof. Specifically, the line member 25 includes a line member body 26 and the connection part 31 provided distal to the line member body 26. The line member body 26 preferably has both flexibility to bend along a shape of a body cavity and rigidity to reliably reach a target site in well balance. As the line member body 26, a metal wire such as a stainless steel and a carbon steel; and a yarn formed from a synthetic resin such as a polyamide resin (for example, nylon), a polyolefin resin (for example, polyethylene or polypropylene), a polyester resin (for example, PET), an aromatic polyether ketone resin (for example, PEEK), a polyimide resin and a fluororesin (for example, PTFE, PFA, ETFE) can be used, for example. The yarn may be a monofilament yarn, a multifilament yarn or a spun yarn.

The connection part 31 is preferably made of a material having biocompatibility, and for example, it is preferably made of a stainless steel such as SUS 303, SUS 304 and SUS 631; Ni—Ti alloy; or the like, as with the clip 22 and the tightening ring 24. The connection part 31 may be made of a synthetic resin such as a polyamide resin (for example, nylon), a polyolefin resin (for example, polyethylene or polypropylene), a polyester resin (for example, PET), an aromatic polyether ketone resin (for example, PEEK), a polyimide resin and a fluororesin (for example, PTFE, PFA, ETFE).

It is preferred that the connection part 31 has directionality in axially-rotation, whereby it can connect with the base end part 23 of the clip 22 in a proper orientation. The axial rotation means rotation around a long axis of the line member 25. Examples of the connection part 31 having directionality in axially-rotation includes, for example, one in which a distal part of the connection part 31 is widely formed in a direction perpendicular to the axis, as shown in FIG. 10. In this case, the connection between the clip 22 and the line member 25 is achieved by engaging the clip 22 with the line member 25 with an opening and closing direction of the clip 22 and an extending direction of the distal part of the connection part 31 being arranged substantially perpendicular or parallel to each other, whereby the connection part 31 can be suitably connected to the clip 22.

It is preferred that the connection part 31 is rotatably connected to the line member body 26. Concerning the "rotatably", the connection part 31 may rotate relative to the line member body 26, or the connection part 31 may be fixed to the line member body 26 and the rotation of the connection part 31 is achieved by twisting the line member body 26.

It is preferred that at least a part of the line member 25 is disposed inside an inner tubular body 27. That is, it is preferred that the clip device 21 comprises the inner tubular body 27 which the line member 25 is disposed inside a lumen thereof. When the clip device 21 is configured in this manner, opening degree of the clip 22 can be adjusted by moving the line member 25 in the proximal direction or the distal direction with respect to the axial direction in using the line member 25 connected with the clip 22. Concerning the adjustment of the opening degree of the clip 22, for example, the clip 22 can be closed when the tightening ring 24 of the clip 22 is moved to the distal part of the clip 22 by moving the line member 25 in the proximal direction relative to the inner tubular body 27 to bring the tightening ring 24 into contact with the inner tubular body 27. Further, the connection part 31 of the line member 25 can be formed so as to be retractable into the inner tubular body 27.

The inner tubular body 27 preferably has both flexibility to bend along a shape of a body cavity and rigidity to reliably reach a target site in proper balance. The inner tubular body 27 can be composed of, for example, a tubular body formed of a coiled metal or synthetic resin, a tubular body rotatably formed by connecting a plurality of short cylindrical joint pieces in the axial direction, or a tubular body made of a synthetic resin.

The clip device 21 may further comprise an outer tubular body, and in this case, the inner tubular body 27 is disposed inside the outer tubular body (not shown in the drawings). The outer tubular body is preferably formed such that the clip 22 is retractable into the outer tubular body in the state where the clip 22 is connected to the line member 25. When the clip device 21 is configured in this manner, it is possible to prevent the clip 22 from damaging the forceps channel in the endoscope or body tissues other than the diseased part during inserting the clip device 21 into the forceps channel from a forceps port of the endoscope and conveying the clip 22 to a tissue to be treated.

The outer tubular body preferably has both flexibility to bend along a shape of a body cavity and rigidity to reliably reach a target site in proper balance. The outer tubular body can be composed of, for example, a tubular body made of a synthetic resin, a tubular body formed of a coiled metal or synthetic resin, or a tubular body rotatably formed by connecting a plurality of short cylindrical joint pieces in the axial direction. As the outer tubular body, a tubular body made of synthetic resin is preferably used, and the outer tubular body is preferably made of a transparent or translucent material so that a user (surgeon) is able to visually check the positional relation between the outer tubular body and the inner tubular body.

In many cases, a plurality of clips 22 are used during one operation, and it is necessary to attach a new clip 22 to the clip device 21 every time each clipping operation is performed. For this reason, it is desirable to attach the clip 22 to the clip device 21 accurately and promptly. However, the clip 22 for medical use is very small and it is difficult to directly attach it by hand. In particular, when a clip device in which the connection part 31 of the line member 25 has directionality in axially-rotation is used as the clip device 21, connecting such connection part 31 to the clip 22 so as to take the orientation properly becomes a very difficult operation.

Therefore, in order to facilitate attaching the clip 22 to the clip device 21, a clip cartridge 1 is used. As shown in FIGS. 1 to 4, a clip cartridge 1 comprises an insertion port 2 for inserting the line member 25, an insertion path 3 extending distally from the insertion port 2, and a storing part 4 for storing the clip 22, that is connected to a distal end of the insertion path 3. In using the clip cartridge, the clip 22 is placed in the storing part 4 and the line member 25 is inserted into the insertion path 3 from the insertion port 2, whereby the connection part 31 provided on the distal part of the line member 25 can be properly connected to the clip 22. In the clip cartridge, a direction toward the insertion port is referred to as a proximal direction and a direction toward a part in which the clip is stored is referred to as a distal direction.

The storing part 4 is a space for storing the clip 22. In FIG. 4, the clip 22 is stored in the storing part 4 in an opened state. The storing part 4 is formed in the clip cartridge such that the base end part 23 (a proximal part of the clip 22) of the clip 22 is positioned to face the insertion path 3. The clip cartridge of the present invention includes both an embodiment in which the clip 22 is stored in the storing part 4 and an embodiment in which the clip 22 is not stored in the storing part 4.

The insertion path 3 is a path for inserting the line member 25, and is formed so as to connect the insertion port 2 and the storing part 4. The insertion path 3 is normally formed so as to extend straight from the insertion port 2 to the storing part 4, and the extending direction of the insertion path 3 corresponds to a direction from the insertion port 2 to an entrance of the storing part 4. On a part of the inner surface of the insertion path 3, a convex part such as a protrusion 5 described later is formed. The protrusion 5 controls an angle of the line member 25 by contact with the line member 25. A concave part may be formed on the inner surface of the insertion path 3 as necessary. The insertion port 2 corresponds to the entrance of the insertion path 3 and is formed on the outer surface of the clip cartridge 1.

The line member 25 to be inserted into the insertion path 3 includes the connection part 31 and the line member body 26; and the length in the long axis direction of the connection part 31 may exceed the length of the insertion path 3, or may be shorter than that of the insertion path 3 and formed such that the connection part 31 and the line member body 26 is inserted into the insertion path 3 with the connection part 31 in the lead.

Figure 5:
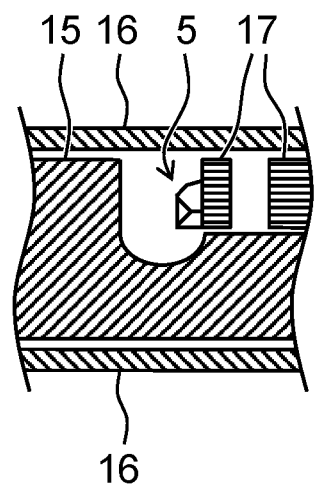
FIG. 5 shows a cross-sectional view taken along a line V-V of the clip cartridge shown in FIG. 1.

FIG. 5 shows a cross-sectional view taken along the line V-V of the clip cartridge shown in FIG. 1, and the cross-section of the insertion path 3 (the cross-section perpendicular to the extending direction of the insertion path 3) is formed so that at least the connection part 31 of the line member 25 is able to pass through it, preferably at least a part of the cross-section is formed in a curved shape. As to the size of the cross-section of the insertion path 3, if the size of the cross-section of the insertion path 3 is too large, the connection part 31 and the protrusion 5 do not properly contact with each other and it becomes difficult to control the direction of the connection part 31 of the line member 25; and therefore, a maximum cross-sectional length of the insertion path 3 at least in a distal half thereof is preferably 2.5 times or less of a maximum cross-sectional length of the connection part 31 (the maximum cross-sectional length perpendicular to the axial direction of the line member 25), more preferably 2.0 times or less of that. Regarding the specific size of the cross-section of the insertion path 3, the maximum cross-sectional length in the distal half of the insertion path 3 is preferably in the range of 0.5 mm to 4.0 mm, for example.

Figure 6:
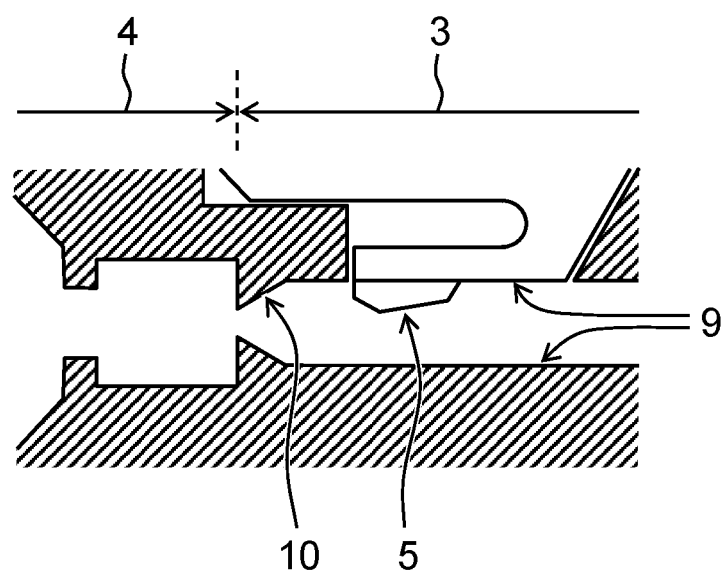
FIG. 6 shows an enlarged plan view in the section from an insertion path to a storing part of the clip cartridge, where a part of which is shown as a cross-sectional view.
Figure 7:
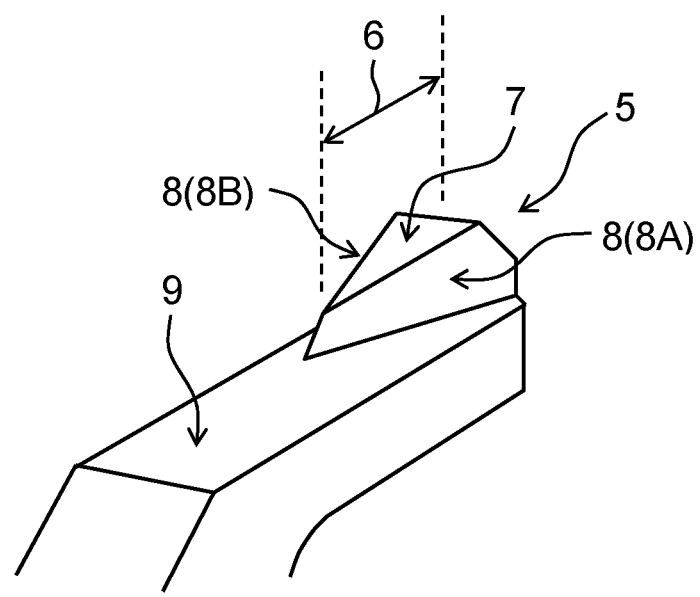
FIG. 7 shows a perspective view of a protrusion.
Figure 8:
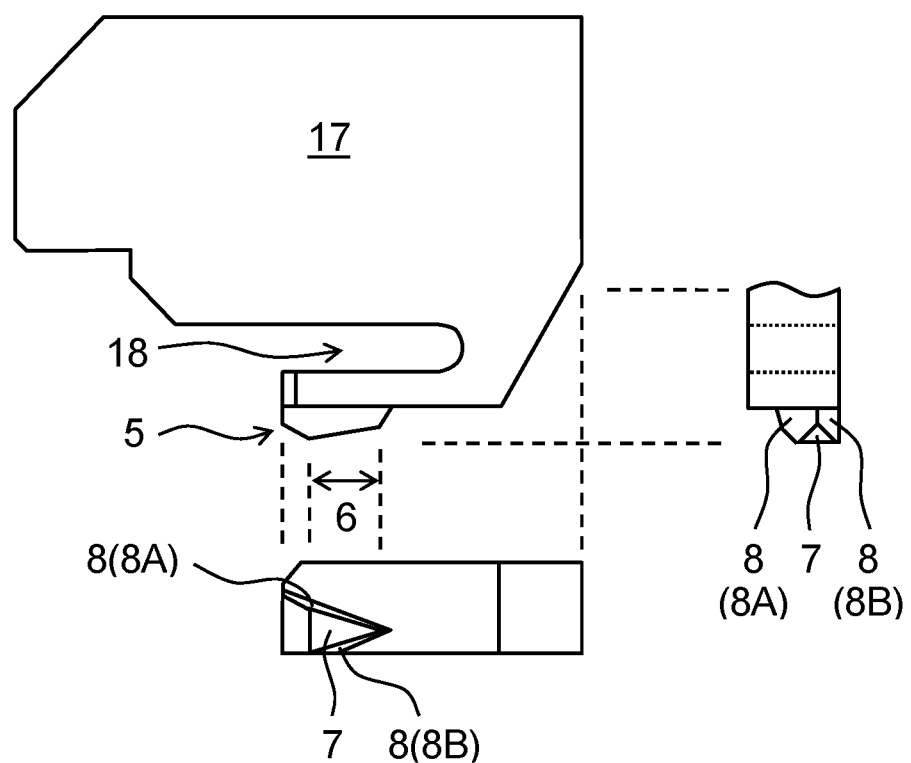
FIG. 8 shows a three-sided view of a regulation member.

The insertion path 3 has a protrusion 5 projecting from the inner surface of the insertion path. The protrusion will be hereinafter described in detail with reference to FIGS. 6 to 8. FIG. 6 shows an enlarged plan view in the section from the insertion path to the storing part of the clip cartridge, FIG. 7 shows a perspective view of the protrusion, and FIG. 8 shows a three-sided view of a regulation member provided with the protrusion. In FIG. 6, the projecting direction of the protrusion corresponds to the lower side of the drawing. In FIG. 7, a perspective view of the protrusion on the regulation member is shown, the projecting direction of the protrusion corresponds to the upper side of the drawing, and the right back side of the drawing corresponds to the distal direction of the insertion path.

The protrusion 5 is formed so as to project from the inner surface 9 of the insertion path into space of the insertion path. It is preferred that a top part of the protrusion 5 is planar. As shown in FIG. 7, the protrusion 5 may have a top surface 7 of which the top part is planar and a lateral surface 8 between the top surface 7 and the inner surface 9 of the insertion path.

The height of the protrusion 5 is not particularly limited as long as the connection part 31 of the line member 25 is formed so as to pass through the insertion path 3 at a part where the protrusion 5 is formed in the insertion path 3; and the protrusion 5 is preferably formed so as to project from the inner surface 9 of the insertion path at a height that does not reach the center or the centroid of the cross-section of the insertion path 3.

The protrusion 5 has a part whose top surface 7 widens toward the distal end and whose height from the inner surface 9 of the insertion path increases toward the distal end, that is referred to as a guide part 6. The protrusion 5 has lateral surfaces 8 provided such that distance therebetween increases toward the distal end; and one of the lateral surfaces 8 is referred to as a first lateral surface 8A, and the other of those is referred to as a second lateral surface 8B. In FIGS. 7 and 8, the top surface 7 of the guide part 6 is formed in a triangular shape, however, the top surface 7 may be formed in any shape such as a trapezoidal shape or the like. Corners of the top surface 7 may be rounded and sides of that may be curved or rounded. When the protrusion 5 has the guide part 6 that is formed such that the top surface 7 widens toward the distal end of the insertion path 3 and the height from the inner surface 9 of the insertion path increase, the connection part 31 of the line member 25 comes into contact with the guide part 6 of the protrusion 5 during insertion of the line member 25 into the insertion path 3, whereby the line member 25 is axially rotated by the guide part 6 and the angle or position of the connection part 31 can be controlled. Any one or a plurality of the angle or the position of the connection part 31 may be controlled.

The above will be described in detail. Since the protrusion 5 has a part (guide part 6) in which the height of the top surface 7 from the inner surface 9 of the insertion path increases toward the distal end of the insertion path 3, the connection part 31 of the line member 25 comes into contact with the guide part 6 while the line member 25 is being inserted into the insertion path 3 and proceeding toward the distal end. At this time, when the distal part of the connection part 31 comes into contact with the top surface 7, the line member 25 is axially rotated so that the distal part of the connection part 31 and the top surface 7 are substantially parallel. By the contact of the connection part 31 with the top surface 7 of the cartridge in this manner, the angle with respect to the axial rotation direction or the position of the connection part 31 can be controlled. Here, the axial rotation means a rotation around the long axis the line member 25. What axially rotates may be the connection part 31, the line member body 26, or both of them. Meanwhile, in the case where the distal part of the connection part 31 is inserted into the insertion path 3 in such a manner that it is deviated in the axial rotation direction (that is, not parallel to the top surface 7) and the distal part of the connection part 31 comes into contact with the lateral surface 8 of the protrusion 5, since the protrusion 5 formed such that the top surface 7 widens toward the distal end of the insertion path 3, the line member 25 easily axially rotates while the connection part 31 proceeds toward the distal end of the insertion path 3 along the lateral surface 8 of the protrusion 5. Thus, while the connection part 31 proceeds toward the distal end of the insertion path 3 along the lateral surface 8 of the protrusion 5, the traveling direction of the connection part 31 is shifted and distortion occurs in the line member 25, and as a result, the line member 25 is likely to be axially rotated so as to eliminate or reduce the distortion and moves to a position where the connection part 31 comes into contact with the top surface 7, and by this contact, the angle with respect to the axial rotation direction or the position of the line member 25 is properly controlled.

The size of the guide part 6 may be appropriately determined according to the size of the connection part 31 and the cross-sectional length of the insertion path 3; and for example, the height of the guide member 6 may be 0.5 mm to 2.0 mm, the width (the width of the distal part) of that may be 0.5 mm to 2.0 mm, and the length (the length in the extending direction of the insertion path) may be 1.0 mm to 3.0 mm.

From the viewpoint that the connection part 31 axially rotates smoothly, a width of the guide part 6 on the proximal part (the insertion port side) is preferably 40% or less of the width of that on the distal part (the storing part side), more preferably 25% or less of that, and even more preferably 10% or less of that. It is also preferable that the shape of the top surface 7 is a triangle (including a triangle with rounded corners). From the same viewpoint, the height of the guide part 6 on the proximal part (the insertion port side) is preferably 80% or less of that on the distal part (the storage section side), more preferably 70% or less of that, and even more preferably 60% or less of that It is preferable that the lateral surfaces 8A, 8B of the protrusion 5 are provided at different angles to the extending direction of the insertion path 3. That is, in the protrusion 5, it is preferred that the angle of the first lateral surface 8A to the extending direction of the insertion path 3 is larger than the angle of the second lateral surface 8B to that. By forming the first lateral surface 8A and the second lateral surface 8B in this manner, the probability of the connection part 31 traveling along the first lateral surface 8A becomes higher than the probability of the connection part 31 traveling along the second lateral surface 8B when the distal part of the connection part 31 hits a proximal tip of the protrusion 5. Therefore, when the line member 25 is inserted into the insertion path 3, the connection part 31 is brought into contact with the protrusion 5, followed by easily proceeding smoothly further to the distal part of the insertion path 3 along the first lateral surface 8A. The line member 25 which has proceeded along the first lateral surface 8A is then axially rotated so that the connection part 31 comes into contact with the top face 7, as described above. The first lateral surface 8A may be located on the right side to the proximal tip of the protrusion 5 as shown in FIG. 7 in the state where the protrusion 5 is viewed from the insertion port 2 side with the top surface 7 as the upper side, or it may be located on the left side to that on the contrary, and thus, it may be located on either side.

The lateral surfaces 8A, 8B may be formed at right angle to the inner surface 9 of the insertion path, or may be formed at an angle of more than 90° to that. In the latter case, the protrusion 5 is formed in a substantially trapezoidal shape (specifically, in the shape of which distance between both lateral surfaces 8A and 8B on the inner surface 9 side of the insertion path is wider than that on the top surface 7 side) in a cross-section perpendicular to the extending direction of the insertion path 3. By forming the lateral surfaces 8A, 8B in this manner, when the distal part of the connection part 31 comes into contact with the lateral surfaces 8A, 8B, the line member 25 is subjected to a force in an axial rotation direction to be easily axially rotated smoothly while the line member 25 proceeds to the distal part of the insertion path 3. The lateral surfaces 8A, 8B are preferably formed such that the angle to the inner surface 9 of the insertion path is 90° or larger and 120° or smaller, more preferably 91° or larger and 115° or smaller.

It is preferable that only one protrusion 5 is provided in the insertion path 3. In the clip cartridge of the present invention, it is possible to properly control the angle with respect to the axial rotation direction and the position of the connection part 31 by providing only one protrusion 5.

The protrusion 5 is preferably provided in the insertion path 3, and more preferably, the space in which the connection part 31 of the line member 25 can be accommodated is secured in the insertion path 3 in a position distal to the protrusion 5. That is, the protrusion 5 is preferably formed in the insertion path 3, away from the entrance of the storing part 4 at least at a distance corresponding the length of the connection part 31. By providing the protrusion 5 in the insertion path 3 in this manner, the connection part 31 is easily connected to the clip 22 in the state where the angle with respect to the axial rotation direction and the position of the connection part 31 are properly controlled by the protrusion 5.

It is preferred that the protrusion 5 is pushable in a direction opposite to a projecting direction thereof. In this case, for example, the protrusion 5 is preferably formed so as to project from the inner surface of the insertion path in a no-load state and is pushable in a direction opposite to the projecting direction by contact with the connection part 31. Here, the protrusion 5 is only required to be pushed in a direction opposite to the projecting direction at least a little when the connection part 31 comes into contact with the protrusion 5, and the it may not be pushed so as to be completely below the inner surface of the insertion path. By forming the protrusion 5 in this manner, when the connection part 31 comes into contact with the protrusion 5, the protrusion 5 is pushed in the direction opposite to the projecting direction so that the traveling direction of the connection part 31 is not shifted a lot and the connection part 31 of the line member 25 can be inserted further to the distal part of the insertion path 3. As a result, it is possible to reliably connect the connection part 31 to an appropriate position of the clip 22. For the push, the protrusion 5 is only required to be moved to the opposite side to the projecting direction thereof relative to the insertion path 3, and the push can be realized by slide of the protrusion 5 or deflection of the protrusion 5 against a cartridge body or a member provided with the protrusion (for example, a regulation member 17).

From the viewpoint of properly controlling the angle with respect to the axial rotation direction and the position of the connection part 31, the protrusion 5 is preferably formed so as to be pushed to the opposite side to the projecting direction and to exert a drag force toward the projecting direction (that is, a drag force toward space of the insertion path) when the connection part 31 is brought into contact with the protrusion 5. Thereby, the connection part 31 can appropriately contact the protrusion 5 and the connection part 31 is easily axially rotated to the proper angle or position. Meanwhile, considering drawing the clip device 21 in which the line member 25 (the connection part 31) is connected to the clip 22 from the clip cartridge 1, the protrusion 5 is preferably configured to be movable in a direction away from the insertion path 3 so as not to cause a large resistance force toward the projecting direction, whereby the protrusion 5 is likely not to be an obstacle when drawing the clip device 21 from the clip cartridge 1.

The protrusion 5 is preferably removable from the insertion path 3. For example, as shown in FIG. 3, the protrusion 5 is formed on a regulation member 17, and the regulation member 17 is slidable upward in the drawing. Removal of the protrusion 5 means that the protrusion 5 is dismounted from the inner surface 9 of insertion path of the cartridge, and the protrusion 5 or a member provided with the protrusion 5 (for example, the regulation member 17) may be separated from the cartridge, or the protrusion 5 or the member provided with the protrusion 5 may be slidable in the cartridge. When the protrusion 5 is formed in this manner, the clip device 21 can be easily taken out from the clip cartridge 1 by removing the protrusion 5 even in the case that the clip device 21 is caught by the protrusion 5 in drawing the clip device 21 from the clip cartridge 1 after connecting the line member 25 with the clip 22. Alternatively, when drawing the clip device 21 from the clip cartridge 1, the protrusion 5 may be removed in advance.

The clip cartridge 1 can be composed of a cartridge body 15 and a cartridge cover 16, wherein the regulation member 17 which is slidable relative to the cartridge body 15 is provided in the cartridge body 15 and the protrusion 5 is provided on the regulation member 17. As shown in FIG. 1, by configuring the protrusion 5 on the regulation member 17 so as to project from the inner surface of the insertion path in the state where the cartridge cover 16 is attached to the cartridge body 15, movement of the regulation member 17 can be restricted. With such a configuration, the clip 22 and the line member 25 can be connected to each other only when the cartridge cover 16 is attached, and when the cartridge cover 16 is detached from the cartridge body 15 after the connection, fixing of the regulation member 17 by the cartridge cover 16 is released and the regulation member 17 including the protrusion 5 can be removed from the insertion path 3 so that the clip device 21 is taken out from the cartridge body 15. With such a configuration, the connection between the clip 22 and the line member 25 can be reliably performed and erroneous operation is prevented.

It is preferred that the insertion path 3 has a tapered part 10 located distal to the protrusion 5 and being narrower in the height direction of the protrusion 5 toward the distal end thereof (refer to FIG. 6). The entrance of the storing part 4 is located distal to the tapered part 10. By forming the tapered part 10 on the distal part of the insertion path 3, the distal part of the connection part 31 fits into the tapered part 10 and the connection part 31 is easily connected to the clip 22 placed in the storing part 4 properly while maintaining its angle and position which has been adjusted by the protrusion 5. That is, when the line member 25 is inserted into the insertion path 3, the connection part 31 comes into contact with the guide part 6 of the protrusion 5 to be set so that the distal part of the connection part 31 is substantially parallel to the top surface 7, and by inserting the connection part 31 into the tapered part 10 in that state, the distal part of the connection part 31 fits so as to conform to the shape of the tapered part 10 and the connection part 31 is set at an appropriate angle or position in relation to the clip 22 stored in the storing part 4.

The tapered part 10 is formed such that the length of the cross-section of the insertion path 3 (the cross-section perpendicular to the extending direction of the insertion path 3) is shortened in one direction toward the distal end thereof, and the tapered part 10 may narrow in a straight line fashion, may narrow in a curved line fashion or may narrows discontinuously. In at least a part of the tapered part 10, the inner surface of the insertion path is preferably formed to have an angle of, for example, 20° or more and 60° or less to the extending direction of the insertion path 3.

The tapered part 10 is preferably provided to be continuous with the entrance of the storing part 4. With such a configuration, the line member 25 can be more reliably connected to the clip 22 while maintaining its angle and position which has been adjusted by the protrusion 5.

The clip cartridge may be composed of one member or may be composed of two or more members. However, the clip cartridge has the insertion path and the storing part formed therein, and from the viewpoint of easily manufacturing thereof, it is preferable that the clip cartridge is composed of two or more members. For example, it is preferable that the clip cartridge 1 includes a cartridge body 15 and a cartridge cover 16, the cartridge body 15 has a groove for forming the insertion path and a recessed part for forming the storing part, and the insertion port 2, the insertion path 3 and the storing part 4 are respectively formed by covering the cartridge body 15 with the cartridge cover 16. Normally, both the insertion port 2 and the insertion path 3 are formed by covering the groove for forming the insertion path with the cartridge cover 16; however, a groove or a recess for forming the insertion port may be separately provided in the cartridge body 15, if necessary. By constructing the clip cartridge in this way, the clip cartridge is easily manufactured, and it becomes easy to set the clip 22 in the clip cartridge 1 and take out the clip device 21 in which the line member 25 is connected with the clip 22 from the clip cartridge 1.

The shape of the cartridge cover 16 is not particularly limited as long as it can cover the groove for forming the insertion path and the recess for forming the storing part of the cartridge body 15. In FIGS. 1 to 3, the clip cartridge 1 is configured such that the cartridge cover 16 is formed in a tubular shape and surrounds the cartridge body 15 with the extending direction of the insertion path 3 as its axis. Alternatively, the cartridge cover may be formed in a plate and configured to overlap with the cartridge body. The surface of the cartridge cover 16 facing the cartridge body 15 may be formed flat, or a groove for forming the insertion path and a recess for forming the storage part may be formed also in the cartridge cover 16.

It is preferred that the clip cartridge 1 comprises the regulation member 17 on which the protrusion 5 is formed, in addition to the cartridge body 15 and the cartridge cover 16. In this case, since the regulation member 17 can be detached from the cartridge body 15 and the cartridge cover 16, it becomes easy to take out the clip device 21 in which the line member 25 is connected with the clip 22 from the clip cartridge 1.

In FIGS. 1 to 3, the regulation member 17 is slidable in a direction substantially perpendicular to the extending direction of the insertion path 3, the cartridge cover 16 is slidable in the extending direction of the insertion path 3, and the slide of the regulation member 17 is controlled by the position of the cartridge cover 16. In the case where the cartridge cover 16 is in a position covering the regulation member 17, the regulation member 17 is fixed to the cartridge body 15 in a state where the protrusion 5 projects from the inner surface of the insertion path. In the case where the cartridge cover 16 is not in the position covering the regulation member 17, the regulation member 17 becomes slidable so that the projecting height of the protrusion 5 from the inner surface of the inserting path can be lowered or the protrusion 5 can be formed not to project from the inner surface of the inserting path. As shown in detail in FIG. 8, it is preferred that a through groove 18 extending in the extending direction of the insertion path 3 is formed in the regulation member 17, whereby the protrusion 5 is formed so as to be pushable as well as it exerts a resistance toward the projecting direction suitably when the protrusion 5 is pushed in a direction opposite to the projecting direction.

Constituent materials of the cartridge body 15, the cartridge cover 16, and the regulation member 17 are not particularly limited; however, they are preferably made of synthetic resin from the viewpoint of facilitating precision machining, maintaining the clip 22 stored therein in a sanitary condition, and preventing the clip 22 from being damaged. In addition, the cartridge cover 16 is preferably made of a transparent or translucent material so that a user (surgeon) can visually check the connection of connecting the clip 22 to the line member 25.

A preferable embodiment of the connection part 31 of the line member 25 will be described with reference to FIG. 10. It is preferred that the connection part 31 has a flat portion 32 on the distal part thereof When the flat portion 32 is formed on the distal part of the connection part 31, the connection part 31 is easily connected to the clip 22 by making the flat portion 32 engage with the base end part 23 of the clip 22. The flat portion 32 is not limited to one in which the surface is formed completely parallel to the axial direction of the line member 25 but includes one in which the surface is formed at an angle within ±10° to the axial direction of the line member 25.

In the clip device 21 and the connection part 31 shown in FIGS. 9 and 10, an opening is formed in the flat portion 32 of the connection part 31, and the connection part 31 is configured to be able to connect to the clip 22 by engaging the base end part 23 of the clip 22 with the opening. The shape of the distal part of the connection part 31 is not limited to the shape shown in the drawings, and for example, the opening of the flat portion 32 may be formed to reach the distal end of the connection part 31. Or, as disclosed in Patent Literatures 1 and 2, the connection part 31 may be formed in a C shape or a hook shape.

It is preferred that the connection part 31 has an inclined portion 33 whose thickness increases toward the proximal end thereof. In the case that the connection part 31 has the inclined portion 33, the connection part 31 is easily axially rotated also by bringing the guide member 6 into contact with the inclined portion 33, when the line member 25 is inserted into the insertion path 3 and the connection part 31 contacts the guide part 6. The inclined portion 33 is formed at an angle of more than ±10° to the axial direction of the line member 25, preferably at an angle of ±20° or more to that.

It is preferred that the connection part 31 is thicker than the line member body 26. By forming the line member 25 in this manner, the connection part 31 easily comes into contact with the protrusion 5 when the line member 25 is inserted into the insertion path 3. In addition, after the connection part 31 has passed the protrusion 5, the connection part 31 can be stably held in a position distal to the protrusion 5 in the insertion path 3 and the connection between the connection part 31 and the clip 22 can be facilitated. It is preferred that the proximal part of the connection part 31 is inclined so as to reduce its diameter toward the line member body 26. This inclination is preferably formed at an angle of 20° or more and 60° or less to the axial direction. When the inclination is formed in this manner, the connection part 31 can be retracted into the inner tubular body 27 without being caught.

With use of the clip cartridge 1, the clip device 21 can be easily manufactured by connecting the clip 22 to the line member 25. For example, the clip device 21 can be manufactured by conducting the steps of: placing the clip 22 in the storing part 4 of the clip cartridge 1; and inserting the line member 25 having the connection part 31 on the distal part thereof into the insertion path 3 of the clip cartridge 1 to connect the connection part 31 to the clip 22. In the clip cartridge 1, the clip 22 may be stored in the storing part 4 in advance. In this case, the method of manufacturing the clip device comprises the step of inserting the line member 25 having the connection part 31 on the distal part thereof into the insertion path 3 of the clip cartridge 1 to connect the connection part 31 to the clip 22.

This application claims priority to Japanese Patent Application No. 2015-233971, filed on Nov. 30, 2015. All of the contents of the Japanese Patent Application No. 2015-233971, filed on Nov. 30, 2015, are incorporated by reference herein.

REFERENCE SIGNS LIST

1: a clip cartridge
2: an insertion port
3: an insertion path
4: a storing part
5: a protrusion
6: a guide part
7: a top surface
8: a lateral surface, 8A: a first lateral surface, 8B: a second lateral surface
9: an inner surface of the insertion path
10: a tapered part
15: a cartridge body
16: a cartridge cover
17: a regulation member
21: a clip device
22: a clip
23: a base end part
24: a tightening ring
25: a line member
26: a line member body
27: an inner tubular body
31: a connection part
32: a flat portion
33: an inclined portion

The invention claimed is:

1. A medical clip cartridge for connecting a medical clip to a connection part of a line member in which the connection part is provided on a distal part of the line member, comprising:
a cartridge body having an insertion port for inserting the connection part of the line member, an insertion path extending distally from the insertion port, and a storing part for storing the clip, that is connected to a distal end of the insertion path; and
a protrusion projecting into the insertion path in a radial direction of the insertion path so that the protrusion is configured to come in contact with the connection part of the line member to be inserted,
wherein the protrusion has a part whose top surface widens toward a distal end thereof and whose height from an inner surface of the insertion path increases toward the distal end,
the protrusion is removable from the cartridge body,
the protrusion has a first lateral surface and a second lateral surface provided such that distance therebetween increases toward the distal end, and
when a distal angle between a first plane including the first lateral surface and a second plane including the second lateral surface is divided into a first angle and a second angle, the first angle between the first lateral surface and an extending direction of the insertion path is larger than the second angle between the second lateral surface and the extending direction of the insertion path.

2. The clip cartridge according to claim 1, wherein the insertion path has only one protrusion.

3. The clip cartridge according to claim 1, wherein the insertion path has a tapered part positioned distal to the protrusion and being narrower in a height direction of the protrusion toward a distal end thereof.

4. The clip cartridge according to claim 1, wherein the protrusion is pushable in a direction opposite to a projecting direction thereof.

5. The clip cartridge according to claim 1, wherein the clip cartridge includes a cartridge body and a cartridge cover,
the cartridge body has a groove for forming the insertion path and a recessed part for forming the storing part, and
the insertion port, the insertion path and the storing part are respectively formed by covering the cartridge body with the cartridge cover.

6. The clip cartridge according to claim 1, wherein the connection part is formed such that a distal part is widened in a direction perpendicular to an axis of the line member.

7. The clip cartridge according to claim 6, wherein the connection part has an inclined portion whose thickness increases toward a proximal end thereof.

8. The clip cartridge according to claim 1, further comprises the clip stored in the storing part.

9. The clip cartridge according to claim 1, wherein the protrusion is provided on a regulation member,
the regulation member is slidably disposed to the cartridge body so that a part of the regulation member defines the inner surface of the insertion path and the protrusion projects from the inner surface of the insertion path, and
the regulation member is slidable in the radial direction of the insertion path so that the regulation member is separated from the cartridge body.

10. The clip cartridge according to claim 1, wherein the protrusion is provided on a regulation member,
the regulation member is slidably disposed to the cartridge body so that a part of the regulation member defines the inner surface of the insertion path and the protrusion projects from the inner surface of the insertion path,
the regulation member is slidable in the radial direction of the insertion path so that the regulation member is separated from the cartridge body, and
the regulation member is provided with a through groove extending from the distal side to the proximal side in the extending direction of the insertion path.

11. The clip cartridge according to claim 1, wherein the protrusion is arranged to be movable in the radial direction of the insertion path so that the protrusion is moved away from the storing part of the cartridge body after the medical clip is connected to the connection part of the line member.

12. The clip cartridge according to claim 1, wherein the storing part has a recessed portion for storing the medical clip, the recessed portion having an opening, through which the medical clip is removed after the medical clip is connected to the connection part of the line member, and
the opening of the storing part faces in a direction perpendicular to the direction in which the protrusion moves away from the storing part of the cartridge body.

13. The clip cartridge according to claim 1, wherein the medical clip has a pair of arms at a distal side, the arms being able to open and close with a fulcrum at a proximal side.

14. A method for manufacturing the medical clip device using the clip cartridge according to claim 1, comprising the steps of:

placing the clip in the storing part of the clip cartridge; and inserting the line member having the connection part on the distal part thereof into the insertion path of the clip cartridge to connect the connection part to the clip.

15. A method for manufacturing the medical clip device using the clip cartridge according to claim 8, comprising the steps of:

inserting the line member having the connection part on a distal part thereof into the insertion path of the clip cartridge to connect the connection part to the clip.

16. A medical clip cartridge for connecting a medical clip for clipping a target site to a connection part of a line member in which the connection part is provided on a distal part of the line member, comprising:

a cartridge body having an insertion port for inserting the connection part of the line member, an insertion path extending distally from the insertion port, and a storing part for storing the clip, that is connected to a distal end of the insertion path;

the medical clip for clipping a target site, the medical clip stored in the storing part, and a protrusion projecting into the insertion path in a radial direction of the insertion path so that the protrusion is configured to come in contact with the connection part of the line member to be inserted, wherein the protrusion has a part whose top surface widens toward a distal end thereof and whose height from an inner surface of the insertion path increases toward the distal end, the protrusion is removable from the cartridge body, the protrusion has a first lateral surface and a second lateral surface provided such that distance therebetween increases toward the distal end, and when a distal angle between a first plane including the first lateral surface and a second plane including the second lateral surface is divided into a first angle and a second angle, the first angle between the first lateral surface and an extending direction of the insertion path is larger than the second angle between the second lateral surface and the extending direction of the insertion path.

17. The clip cartridge according to claim 16, wherein the protrusion is arranged to be movable in the radial direction of the insertion path so that the protrusion is moved away from the medical clip stored in the storing part of the cartridge body after the medical clip is connected to the connection part of the line member.

18. The clip cartridge according to claim 16, wherein the storing part has a recessed portion for storing the medical clip, the recessed portion having an opening, through which the medical clip is removed after the medical clip is connected to the connection part of the line member, and the opening of the storing part faces in a direction perpendicular to the direction in which the protrusion moves away from the medical clip stored in the storing part.

19. The clip cartridge according to claim 16, wherein the medical clip has a pair of arms at a distal side, the arms being able to open and close with a fulcrum at a proximal side.

\* \* \* \* \*